United States Patent [19]

Hawk et al.

[11] Patent Number: 4,476,727
[45] Date of Patent: Oct. 16, 1984

[54] METHOD OF MATERIALS TESTING

[76] Inventors: Marion N. Hawk, 6304 N. Askew, Kansas City, Mo. 64118; James P. Lewis, 7803 Aleta Dr., Spring, Tex. 77060

[21] Appl. No.: 408,940

[22] Filed: Aug. 17, 1982

[51] Int. Cl.³ .................... G01N 3/22; G01N 29/04
[52] U.S. Cl. .................................... 73/847; 73/848; 73/801; 73/786
[58] Field of Search .............. 73/847, 848, 801, 786, 73/587, 841, 845, 761

[56] References Cited

U.S. PATENT DOCUMENTS

| | | | |
|---|---|---|---|
| 1,327,838 | 1/1920 | Naylor | 73/847 |
| 3,460,380 | 8/1969 | Furr | 73/847 |
| 3,759,090 | 9/1973 | McFaul et al. | 73/801 |
| 3,969,960 | 7/1976 | Pagano | 73/761 |
| 4,014,208 | 3/1977 | Moore et al. | 73/761 |

Primary Examiner—Anthony V. Ciarlante

[57] ABSTRACT

A method of measuring a characteristic of a material in a structure is the subject of the present invention. A known stress relationship $S = TC/J$ is utilized in practicing the method of the present invention. In the foregoing formula $S$=strength in p.s.i.; $T$=torque force in pounds/inch; $C$=distance to the point of interest in inches; and $J = \pi/2r^4$ where J is the polar moment of inertia for a circle of radius r (in inches). A drive head is adhesively secured to a segment of the structure to be tested. A known torque force is then applied to the drive head and this known force is translated into a measurement of the material characteristic utilizing the formula indicated. The method may be utilized to test the ultimate shear strength by failing the material or may be utilized to measure strength up to a design criteria without carrying the material to failure. Other material characteristics may also be measured utilizing the known formula set forth above and other known relationships.

6 Claims, 6 Drawing Figures

U.S. Patent — Oct. 16, 1984 — 4,476,727
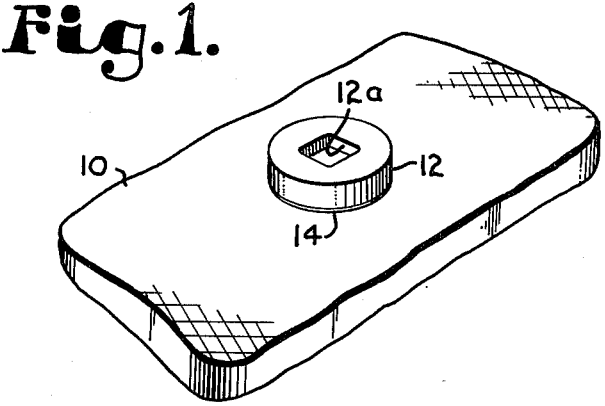
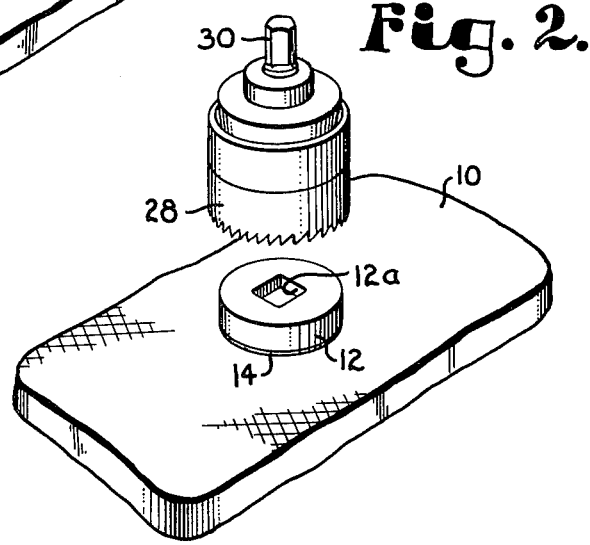
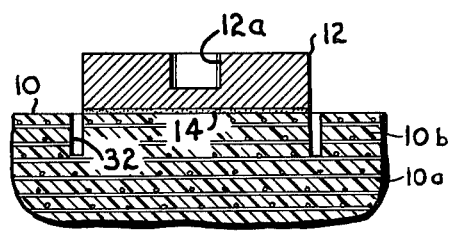
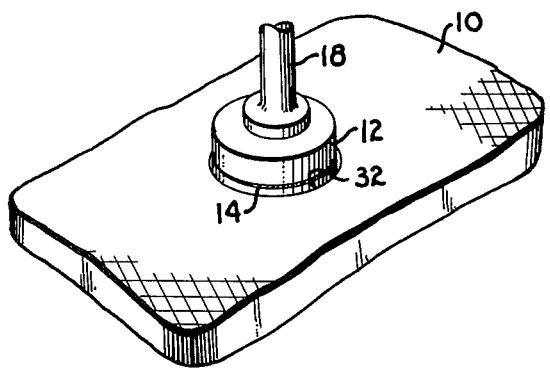
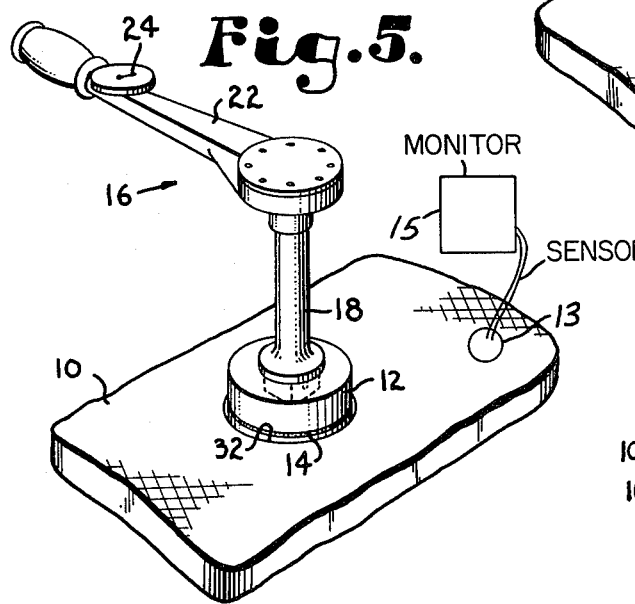
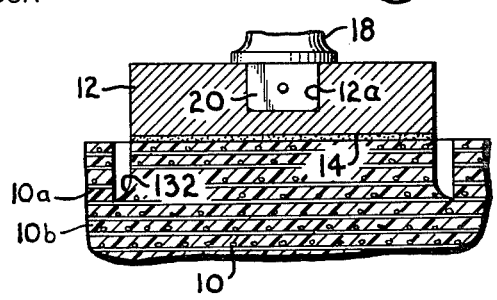

METHOD OF MATERIALS TESTING

This invention relates generally to materials testing and, more particularly, to a method of stress testing of a material without subjecting the entire structure of which the material is a part to the testing forces.

In many instances a particular structure is too large to be tested in its entirety or it is coupled with other structures which make testing unfeasible or it is buried in the ground making access difficult. In these instances, structures have heretofor been tested by removing a section of the structure, subjecting it to appropriate testing forces and then repairing the structure from which the section was taken. The prior testing methods are readily applicable to homogenous materials which have uniform properties throughout. The prior methods are not, however, reliable when dealing with composite materials. Composite materials are finding wider application because of their superior strength and versatility. In particular, composite materials may be easily engineered to meet the specifications required for a particular application. Typical composite materials include glass fibers and polyester, graphite and aluminum, boron and epoxy. Materials of this type cannot be reliably strength tested by taking a section of the material and subjecting it to testing forces. The unrealiability of the prior testing techniques is related to the fact that the reinforcing laminate within the material distributes stresses over the structure and the strength of the entire structure cannot be properly represented by a segment of the structure to which the same forces are applied.

The present invention applies known relationships of material characteristics to stress testing of structures so as to provide an accurate indication of the strength of the structure.

It is therefore a primary object of the present invention to provide a method of stress testing of materials whereby the strength of a structure may be determined without subjecting the entire structure to testing forces.

Another object of the present invention is to provide a method of stress testing for determining the strength of a structure wherein the method is nondestructive of the structure even when the test is carried to the failure point.

As a corollary to the foregoing objects, an important aim of our invention is to provide a method of stress testing which is applicable to the structures made of composite materials and which will provide an accurate indication of the strength of the structure before the material reaches the failure point.

Still another of the objectives of our invention is to provide a method as set forth in the foregoing aims and objects which can be performed by a relatively unskilled technician utilizing readily available equipment.

Other objects of the invention will be made clear or become apparent from the following description and claims when read in light of the accompanying drawing wherein:

FIG. 1 is a perspective view of a material to be tested with a drive head adhesively secured;

FIG. 2 is a perspective view illustrating the manner of isolating that portion of the material to which a testing force is to be applied;

FIG. 3 is a vertical cross-sectional view on an enlarged scale showing the drive head in place on the material being tested;

FIG. 4 is another perspective view of the assembly shown in FIG. 3;

FIG. 5 illustrates the manner of applying a torque force to the drive head to obtain an indication of the strength of the material;

FIG. 6 illustrates the configuration of an alternative form of groove which may be cut when carrying out the test method of the invention.

The method of the present invention utilizes the relationship between stress of a material and the torque force applied to the material as represented by the formula.

$$S = TC/J$$

where
- $S$ = strength in psi
- $T$ = torque force in pounds/inch
- $C$ = distance to the point of interest in inches
- $J = \pi/2r^4$ where $J$ is the polar moment of inertia for a circle or radius $r$ ($r$ in inches)

The composite material shown in FIG. 1 is designated by the number 10 and it is to be understood that such material typically would form the part of a structure (not shown) which is to be tested. Material 10 is not removed from the structure but is indicative only of that portion of the structure on which the testing is performed. For example, material 10 could constitute a section of a large diameter underground pipe. As best illustrated in FIGS. 3 and 6, material 10 is a composite of layers of woven fiberglass 10a and polyester resin 10b. Multiple layers of fiberglass 10a are disposed throughout the material. A drive head in the form of a disc 12 is secured to material 10 by an adhesive layer which has been designated by the number 14. Drive head 12 is provided with opening 12a for receiving the drive shaft of a torque wrench 16 best shown in FIG. 5. Torque wrench 16 includes drive shaft 18 having a drive head 20 which is complementally received by opening 12a. A torque lever mechanism mounts a laterally extending force arm 22 having a torque gauge 24.

The material testing technique of the present invention includes first securing drive head 12 to a segment of the body of material 10 to be tested. Numerous adhesives presently on the market develop a shear strength which is greater than that to be expected of most composite materials. Adhesive strengths in excess of 5,000 psi are not uncommon. A suitable adhesive material for the particular application is selected and drive head 12 is placed at the location where the material strength is to be measured. The segment of material beneath drive head 12 is then isolated utilizing a circular cutter 28 driven through shaft 30 by an appropriate prime mover (not shown). Cutter 28 is utilized to cut a groove 32 around a segment of material 10. Groove 32 is cut to whatever depth it is desired to test material 10.

Once groove 32 is completed, torque wrench 16 is placed on drive head 12 and a desired amount of torque is applied. The test may be to a predetermined design criteria or may proceed to failure. In the former case, a previously calculated design maximum is obtained by applying a known torque force to wrench 16. The formula previously set forth may then be utilized to determine the strength of material in pounds per square inch. If it is desired to carry the test through to failure, the torque force is increased until the failure point is reached. The formula may then be utilized to determine the ultimate strength of the material. The aforedescribed technique may be utilized to test material 10 at different points throughout its thickness. Groove 32 is cut to the level of a particular laminate which is desired to be tested. Successive tests may be conducted at different thicknesses to obtain comparative data on the relative strength of a structure throughout its thickness. Utilizing this technique, it is possible to measure a secondary or tertiary bond within the material.

In an alternative embodiment of the invention, it is possible to utilize acoustic or ultrasonic sound detection equipment to determine the strength of the material 10. A highly sensitive sensor 13 is placed adjacent to the isolated segment being tested and coupled with appropriate monitoring equipment 15 of a type well known to those skilled in the art. The monitoring equipment will register a pattern based upon the distortion which occurs in the material as it is stressed. The emission will increase at least linearly until the failure point is imminent. The pattern of acoustic emissions may also be compared with similar patterns for known samples of the same or similar materials to obtain a value for the strength of the material. When the acoustic emission technique is to be utilized, it is not necessary that a segment of the material be isolated by cutting groove 32. An advantage of utilizing the acoustic emission technique for determining strength is that it requires no destruction of the material being tested and does only minimal damage to the structure. This is because any known material will exhibit non-linear progression of the acoustic emission at a point prior to the ultimate failure point. Some micro damage will occur up to this point, but macro damage will not be experienced.

A particular advantage of the present invention, even when a groove is cut in the material and the torque is increased to material failure, is the relatively small diameter damaged segment can be readily repaired with a high degree of reliability. This is to be contrasted with other testing methods where a much larger segment of the material being tested is removed causing much more extensive repair of a much less reliable nature. Utilizing known formulations, the shear strength value obtained according to the method of the present invention can be utilized to determine the ultimate overall strength of the body of material being tested.

It has been determined that a stress riser effect is present at the bottom of groove 32. This results in a local apparent decrease in strength of the material being tested of 15–25% in this area. Correction for this effect can, of course, be made on a mathematical basis. Alternatively, the stress riser effect may be eliminated by utilizing a cutter blade configuration to provide a groove 132 as shown in FIG. 6. While the invention may be used with various types of materials, it has particular application and advantages with composite materials such as 10 where the properties of the individual components vary over a wide range.

We claim:

1. A method of measuring the structural strength of a material which comprises at least a portion of a structure without subjecting the entire structure to testing forces, said method comprising the steps of:
   isolating a small segment of said material;
   adhesively securing a drive head to said isolated segment;
   applying a known torque force to said drive head; and
   translating said known torque force into a measurement of said structural strength.

2. A method as set forth in claim 1, wherein is included the step of acoustically monitoring said material while said torque force is applied.

3. A method as set forth in claim 2, wherein said step of acoustically monitoring includes observing the indicated yield point of said material.

4. A method as set forth in claim 1, wherein said step of applying a torque force comprises continually increasing said torque force until said material fails.

5. A method as set forth in claim 4, wherein is included the step of acoustically monitoring said material while said torque force is applied and observing the acoustically indicated yield point prior to failure.

6. A method as set forth in claim 1, wherein said structure is comprised of a composite material.

* * * * *